United States Patent [19]

Roszkowski et al.

[11] 4,349,549
[45] Sep. 14, 1982

[54] ANTI-HYPERTENSIVE 1-SUBSTITUTED SPIRO(PIPERIDINE-OXOBENZOXAZINE)S

[75] Inventors: Adolph P. Roszkowski, Saratoga; Robin D. Clark, Palo Alto; Arthur F. Kluge, Los Altos, all of Calif.

[73] Assignee: Syntex (U.S.A.) Inc., Palo Alto, Calif.

[21] Appl. No.: 264,779

[22] Filed: May 18, 1981

[51] Int. Cl.³ .................. A61K 31/535; C07D 498/10
[52] U.S. Cl. ............................ 424/248.55; 424/248.5; 544/71
[58] Field of Search ..................... 544/71; 424/248.54

[56] References Cited
U.S. PATENT DOCUMENTS 3,720,670  3/1973  Nakanishi et al. ................... 544/71
4,224,333  9/1980  Clemence et al. .................. 424/267

Primary Examiner—Henry R. Jiles
Assistant Examiner—Bernard Dentz
Attorney, Agent, or Firm—Annette M. Moore; Kate H. Murashige; Tom M. Moran

[57] ABSTRACT

Novel compounds of the formula:

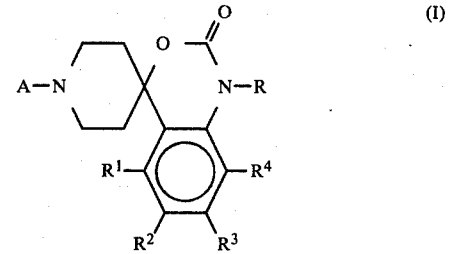

and the pharmaceutically acceptable acid addition salts thereof, wherein $R^1$, $R^2$, $R^3$ and $R^4$ are each independently hydrogen, hydroxy, lower alkyl, lower alkoxy or halo;

R is hydrogen or lower alkyl; and

A is selected from the group consisting of:

2-(benzodioxan-2-yl)-2-hydroxyethyl;

ω-(benzodioxan-2-yl)-alkyl (1–4);

3-(aryloxy)-2-hydroxypropyl, wherein aryloxy is phenyloxy optionally substituted by 1–3 moieties selected from the group consisting of lower alkyl, lower alkoxy, halo, alkylsulfamido, lower alkoxycarbonyl, cyano and trifluoromethyl;

ω-arylalkyl (1–4), wherein aryl is phenyl optionally substituted by 1–3 moieties selected from the group consisting of lower alkyl, lower alkoxy, halo, alkylsulfamido, lower alkoxycarbonyl, cyano and trifluoromethyl;

ω-aryl-ω-oxoalkyl (1–4), wherein aryl is as herein defined;

ω-aryl-ω-hydroxyalkyl (1–4), wherein aryl is as herein defined; and

ω-arylalkyl (1–4), wherein aryl is as herein defined, are useful as antihypertensives.

32 Claims, No Drawings

ANTI-HYPERTENSIVE 1-SUBSTITUTED SPIRO(PIPERIDINE-OXOBENZOXAZINE)S

BACKGROUND OF THE INVENTION

1. Field of the Invention

High blood pressure is a widespread condition which has become, especially in recent years, the object of intensive concern and effort with respect to alleviating the life-threatening effects of its presence. The invention herein concerns a class of 1-substituted spiropiperidine heterocycles which are effective in the central nervous system (CNS) and are useful in treating hypertension.

2. Background of the Invention

It has become clear that at least some of the factors controlling blood pressure reside in the CNS. By altering the state of the receptors for adrenergic compounds through providing compounds suitable for binding at these sites, outcomes such as vasodilation or constriction, heartbeat rate acceleration or slowdown, and heart blood vessel pressure changes can be effected.

The compounds of the present invention have been shown to lower blood pressure. These compounds are spiro[piperidine-oxobenzooxazine]s. The literature describes certain other compounds with superficially similar structures, different from the compounds of this invention. For example, U.S. Pat. No. 4,224,333, issued Sept. 30, 1980 discloses 2-(benzodioxan-2-yl)-2-hydroxyethylpiperidines; substituted with 2H-indol-2-ones at the 4-position of the piperidine ring, as antihypertensives.

SUMMARY OF THE INVENTION

The invention herein concerns novel compounds of the formula:

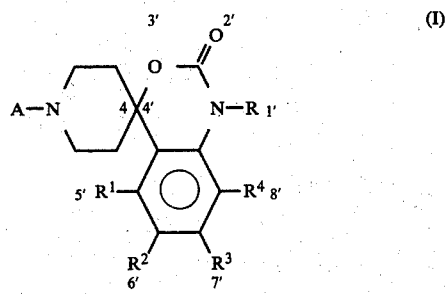

and the pharmaceutically acceptable acid addition salts thereof, wherein $R^1$, $R^2$, $R^3$ and $R^4$ are each independently hydrogen, hydroxy, lower alkyl, lower alkoxy or halo;

R is hydrogen or lower alkyl; and

A is selected from the group consisting of: 2-(benzodioxan-2-yl)-2-hydroxyethyl;

ω-(benzodioxan-2-yl)-alkyl (1–4);

3-(aryloxy)-2-hydroxypropyl, wherein aryloxy is phenyloxy optionally substituted by 1–3 moieties selected from the group consisting of lower alkyl, lower alkoxy, halo, alkylsulfamido, lower alkoxycarbonyl, cyano and trifluoromethyl;

ω-arylalkyl (1–4), wherein aryl is phenyl optionally substituted by 1–3 moieties selected from the group consisting of lower alkyl, lower alkoxy, halo, alkylsulfamido, lower alkoxycarbonyl, cyano and trifluoromethyl;

ω-aryl-ω-oxoalkyl (1–4), wherein aryl is as herein defined;

ω-aryl-ω-hydroxyalkyl (1–4), wherein aryl is as herein defined; and

ω-aryloxyalkyl (1–4), wherein aryloxy is as herein defined.

The compounds of Formula I are antihypertensives. Therefore, in two other aspects, the invention concerns a method for lowering blood pressure in mammals, and pharmaceutical compositions useful for this purpose, which method and compositions employ compounds of Formula I.

In a fourth aspect, the invention concerns methods of preparing the compounds of Formula I.

DETAILED DESCRIPTION OF THE INVENTION

As used herein:

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Lower alkyl" means a branched or unbranched saturated hydrocarbon chain of 1–4 carbons, such as, for example, methyl, ethyl, n-propyl, i-butyl and the like.

"Lower alkoxy" means the substituent —OR wherein R is lower alkyl as defined herein.

"Halo" refers to fluoro, chloro or bromo.

"Optional" or "optionally" means that the subsequently described event or circumstance may or may not occur, and that the description includes instances where said event or circumstance occurs, and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Substituted phenyl" as used herein means that one or more hydrogens of the phenyl ring are replaced by moieties selected from the group consisting of lower alkyl, lower alkoxy, halo, alkylsulfamido, lower alkoxycarbonyl, cyano, and trifluoromethyl. In the context of the present invention, said replacement may be at any position of the phenyl ring.

The moieties represented by A in the compound herein are as follows:

2-(benzodioxan-2-yl)-2-hydroxyethyl represents

ω-(benzodioxan-2-yl)-alkyl represents

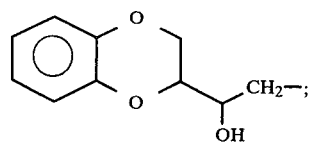

(n = 1-4)

3-(aryloxy)-2-hydroxypropyl represents

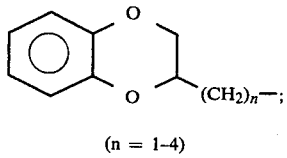

wherein

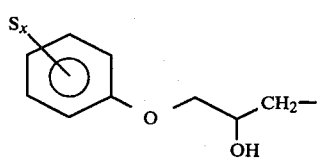

represents phenyl optionally substituted by moieties selected from the group consisting of lower alkyl, lower alkoxy, halo, alkylsulfamido, lower alkoxycarbonyl, cyano and trifluoromethyl, as hereinabove defined;
ω-aryloxyalkyl represents

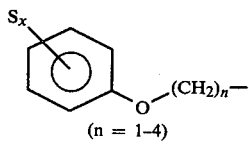

(n = 1-4)

wherein

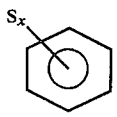

is as herein defined;
ω-aryl-ω-oxoalkyl represents

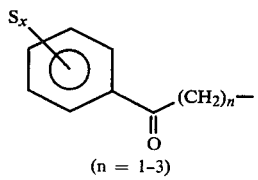

(n = 1-3)

wherein

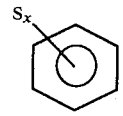

is as herein defined
ω-aryl-ω-hydroxyalkyl represents

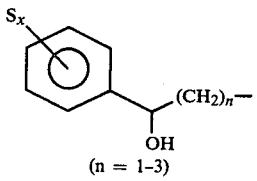

(n = 1-3)

wherein

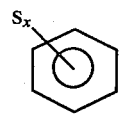

is as herein defined; and
ω-arylalkyl represents

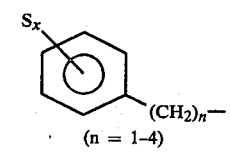

(n = 1-4)

wherein

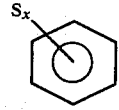

is as herein defined.
Thus, in general, "aryl" represents

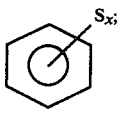

and "aryloxy" represents

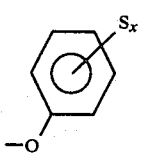

wherein $S_x$ represents substitution as herein defined.

GENERAL METHODS OF PREPARATION

All of the compounds of the invention are prepared by employing the general approach shown in Reaction Scheme I.

REACTION SCHEME I

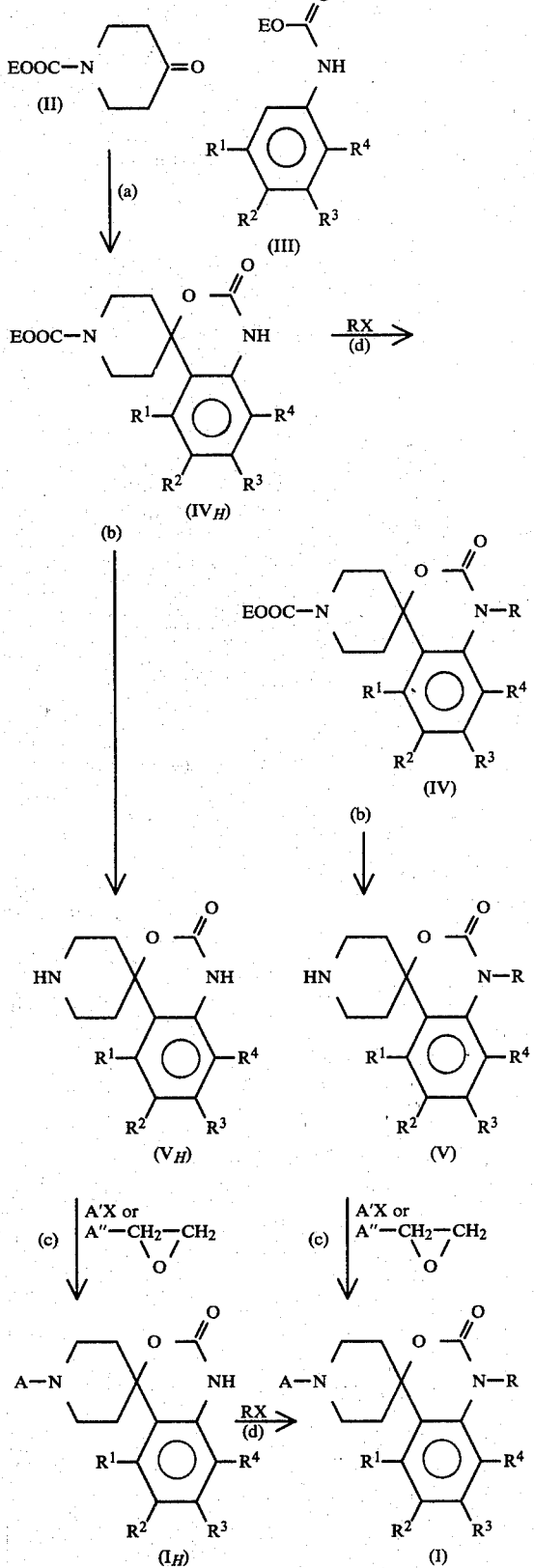

(E represents an alkyl group in an ester linkage with the carboxyl group shown. t-Butyl is the most preferred among such esterifying alkyl groups. X represents a leaving group such as, for example, a halide or sulfonic acid ester; preferably a halide. The subscript "H" below the number of a formula designates the forms of the compound wherein R is hydrogen).

A' represents the subclass of embodiments of A which is the group consisting of ω-(benzodioxan-2-yl)alkyl, ω-aryloxyalkyl, ω-arylalkyl, and ω-aryl-ω-oxoalkyl;

A" represents a radical selected from the group consisting of benzodioxan-2-yl, and aryloxymethyl.

(An additional step is required to prepare those compounds wherein A is ω-aryl-ω-hydroxyalkyl: by reducing the corresponding ω-aryl-ω-oxoderivative).

The starting materials of formulas II and III, A'X,

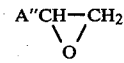

and RX are commercially available or may be prepared by standard methods. A particularly useful method of preparing the benzodioxanyl ethyl epoxides is described in U.S. Pat. No. 4,212,808.

Isolation and purification of the compounds and intermediates described can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

The salt products are also isolated by conventional means. For example, the reaction mixtures may be evaporated to a dryness, and the salts can be further purified by conventional methods.

Those compounds of the invention wherein A is 2-(benzodioxan-2-yl)-2-hydroxyethyl, ω-(benzodioxan-2-yl)alkyl, 3-(aryloxy)-2-hydroxypropyl, and ω-aryl-ω-hydroxy alkyl contain at least one chiral center—i.e. the 2-position of the benzodioxanyl moiety and/or the carbon bearing the hydroxy group.

Accordingly, the compounds of the present invention may be prepared in either optically active form or as racemic mixtures. Unless otherwise specified, the compounds described herein are all in the racemic form. However, the scope of the subject invention herein is not to be considered limited to the racemic forms, but to encompass the individual optical isomers of the compounds.

In those embodiments wherein A is 2-(benzodioxan-2-yl)-2-hydroxyethyl, the compounds of the invention may also exist as mixtures of diastereomers (erythro and threo) since both the benzodioxanyl and hydroxyl substituents are present and there are thus two chiral centers. The diastereomers can, of course, be separated by the aforementioned standard separation techniques; however, the scope of the invention herein includes each of the four individually optically pure forms, and also racemic mixtures of each enantiomeric pair, and mixtures of erythro and threo.

A further limitation is that in those embodiments wherein $R^4$ is hydrogen, and $R^1$ and $R^3$ are not identical to each other, mixtures may result from step (a) of Reaction Scheme I; i.e. R$^1$, for example, may end up in either position 5' or 7' of the spiro compound. Mixtures of such isomers may then be separated by conventional means.

In carrying out step (a) of Reaction Scheme I, the compound of Formula III, preferably that wherein E represents a tertiary butyl moiety, is first treated with a strong base such as a metal hydride or a metal alkide, preferably tertiary butyl lithium, in the presence of an inert aprotic solvent such as for example, tetrahydrofuran (THF) dimethylformamide (DMF) or dimethylsulfoxide (DMSO) preferably DMF. An excess of the base is used, about 1.5–4 moles of base to 1 mole of the compound of Formula III, preferably 1.5–2 moles of base. The reaction is kept at a temperature of about 0° to −70° preferably −20° to −70° for about 0.5–3 hours preferably 1–2 hours.

The compound of Formula II, preferably that wherein E represents a tertiary butyl ester, is then added dropwise until an approximately stoichiometric amount is added to the reaction mixture as prepared in the previous paragraph, over a period of about 5–60 minutes, preferably about 10 minutes at a temperature of about −20° to −70° C., preferably about −70° C.

The compound of Formula IV$_H$ may be isolated if desired, or the reaction mixture treated directly with a deprotecting agent to remove the alkoxycarbonyl moiety from the nitrogen to give V$_H$. The deprotection is carried out under acid conditions by methods known in the art.

The compounds of either Formula I$_H$ or IV$_H$ may be alkylated by treating with a suitable alkyl halide in a molar excess of about 1.2–5 moles alkyl halide to substrate compound, preferably 1.5–2 molar excess, for about 1–5 hours at about 25°–100° C. Formula I$_H$ or IV$_H$ must be preliminarily treated with strong base, such as for example, an alkali metal halide prior to the alkyl halide treatment step. [Step(s) (d)].

The deprotected form of the compound, formula V (or V$_H$) is treated with a suitable epoxide or halide in a manner substantially analogous to that described in U.S. Pat. No. 4,224,333, incorporated herein by reference. In this procedure, with respect to the epoxide, the substrate spiro[piperidine-4,4'-2'-oxo-3',1'-benzooxazine] and the appropriate epoxide, in approximately equimolar ratio, are dissolved in a solvent of appropriate polarity such as alcohol hydrocarbon mixtures for example, methanol/benzene, methanol/toluene, or ethanol/toluene, preferably methanol/toluene. The solution is then cooled to about −10° C. to +50° C., preferably +5° C. to +10° C. and the resulting compound of formula I$_H$ or I is then precipitated. With respect to the halide, the substrate spiro[piperidine-4,4'-2'-oxo-3',1'-benzooxazine] and the appropriate bromide or chloride in approximately equimolar ratio, is dissolved in a nonprotic, mildly basic solvent, formed from an aprotic solvent and a tertiary amine such as, for example, dimethylformamide/triethylamine, tetrahydrofuran/triethylamine or dimethylformamide/pyridine, preferably dimethylformamide/triethylene amine. The mixture is then heated to about 40° to about 100° C., preferably 55° to 65° for about 2 hours to 10 hours, preferably 4 to 6 hours. The mixture is then quenched with water, and the product extracted into an organic solvent. In either case, the resulting compound of Formula I may be isolated by conventional means.

PREFERRED EMBODIMENTS

Preferred embodiments of the compounds of the invention are those wherein R$^1$, R$^2$, R$^3$, and R$^4$ are selected from the group consisting of hydrogen, hydroxy, methoxy and halo, and wherein R is selected from the group consisting of the group hydrogen or methyl. Particularly preferred are those compounds selected from the group consisting of:

1-[2-(benzodioxan-2-yl)-2-hydroxyethyl]-1'-methyl-spiro[piperidine-4,4'-2'-oxo-3',1'-benzooxazine];

1-[2-(benzodioxan-2-yl)-2-hydroxyethyl]-spiro[piperidine-4,4'-2'-oxo-3',1'-benzooxazine];

6'-chloro-1-[2-(benzodioxan-2-yl)-2-hydroxyethyl]-spiro[piperidine-4,4'-2'-oxo-3',1'-benzooxazine];

6'-fluoro-1-[2-(benzodioxan-2-yl)-2-hydroxyethyl]-spiro[piperidine-4,4'-2'-oxo-3',1'-benzooxazine];

1-(benzodioxan-2-ylmethyl)-spiro[piperidine-4,4'-2'-oxo-3',1'-benzooxazine];

1-(2-benzodioxan-2-yl)ethyl)-spiro[piperidine-4,4'-2'-oxo-3',1'-benzooxazine];

5'-hydroxy-1-[2-(benzodioxan-2-yl)-2-hydroxyethyl]-spiro[piperidine-4,4'-2'-oxo-3',1'-benzooxazine];

5'-methoxy-1-[2-(benzodioxan-2-yl)-2-hydroxyethyl]-spiro[piperidine-4,4'-2'-oxo-3',1'-benzooxazine];

1-(2-(2,4-dimethoxyphenoxy)ethyl)-spiro[piperidine-4,4'-2'-oxo-3',1'-benzooxazine];

1-(2-phenoxyethyl)-spiro[piperidine-4,4'-2'-oxo-3',1'-benzooxazine];

1-[3-(2-cyanophenoxy)-2-hydroxypropyl]-spiro[piperidine-4,4'-2'-oxo-3',1'-benzooxazine];

1-[3-phenoxy-2-hydroxypropyl]spiro[piperidine-4,4'-2'-oxo-3',1'-benzooxazine];

7'-fluoro-1-(3-(2-methoxyphenoxy)-2-hydroxypropyl)-spiro-[piperidine-4,4'-2'-oxo-3',1'-benzooxazine];

1-[3-(2-methoxyphenoxy)-2-hydroxypropyl]-spiro[piperidine-4,4'-2'-oxo-3',1'-benzooxazine];

1-[2-phenyl-2-oxoethyl]-spiro[piperidine-4,4'-2'-oxo-3',1'-benzooxazine];

1-[4-(4-fluorophenyl)-4-oxo-n-butyl]-spiro[piperidine-4,4'-2'-oxo-3',1'-benzooxazine];

1-[2-phenyl-2-hydroxyethyl]-spiro[piperidine-4,4'-2'-oxo-3',1'-benzooxazine];

1-[2-(4-hydroxy-3-methoxycarbonylphenyl)-2-hydroxyethyl]-spiro[piperidine-4,4'-2'-oxo-3',1'-benzooxazine];

1-[2-(3-methanesulfamidophenyl)ethyl]-spiro[piperidine-4,4'-2'-oxo-3',1'-benzooxazine];

1-[2-phenylethyl]spiro[piperidine-4,4'-2'-oxo-3',1'-benzooxazine];

1-(2,6-dichlorobenzyl)-spiro[piperidine-4,4'-2'-oxo-3',1'-benzooxazine].

UTILITY AND ADMINISTRATION

The compounds of the invention lower blood pressure in standard tests, and, accordingly, are useful in ameliorating essential hypertension. These compounds, when injected intravenously or intraarterially into the CNS into cats, exhibit an activity similar to clonidine, a well-known $\alpha_2$-antagonist. Additionally, these compounds have been shown to relieve hypertension in spontaneously hypertensive rats (SHR)s when administered orally.

Accordingly, two other aspects of the invention relate to pharmaceutical compositions containing the compounds of this invention, and to methods of ameliorating hypertension using said compounds and said compositions. Administration of the active compounds and salts described herein can be via any of the accepted modes of administration for antihypertensive agents. These methods include oral and intravenous modes, preferably oral administration. Intravenous administration would preferably be reserved for crisis situations, wherein the subject is unable to swallow or administer the medication to himself.

Depending on the intended mode, the compositions may be in the form of solid, semi-solid or liquid dosage forms, such as, for example, tablets, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

The amount of active compound administered will, of course, be dependent on the subject being treated, the severity of the affliction, the manner of administration and the judgment of the prescribing physician. However, an effective dosage is in the range of about 0.0001 to 50 mg/kg/day, preferably 0.001 to 10 mg/kg/day if taken orally. For an average 70 kg human, this would amount to 0.007 to 3500 mg per day, or preferably 0.07 to 700 mg/day, if taken orally.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s) in an amount effective to alleviate the symptoms of the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 0.1%–95% active ingredient, preferably 1–70%.

For intravenous injections, the compound is dissolved in aqueous medium, buffered to the proper pH and formed to control isotonicity for injection.

The following examples serve to illustrate the invention. They should not be construed as narrowing it, or limiting its scope.

PREPARATION 1

Spiro[piperidine-4,4'-2'-oxo-3',1'-benzooxazine]

A 2.0 M solution of 198 ml t-butyllithium n-pentane was added slowly to a −78° C. solution containing 34.7 g of N-t-butoxycarbonylaniline in 250 ml of THF. After 15 minutes at −78° C., the solution was allowed to warm to −20° C. where it was maintained for 2.5 hours. The solution was again cooled to −78° C. and a solution of 34.6 g of N-t-butoxycarbonyl-4-piperidone in 100 ml THF was added. The mixture was allowed to warm to room temperature and was stirred overnight. Ether (250 ml) was added and the mixture was washed with 5% aqueous hydrochloric acid, water, and brine, dried over $Na_2SO_4$, and evaporated. Chromatography of the residue on silica gel with 40% ethyl acetate-hexane afforded 25.7 g of white solid, t-butoxycarbonyl-protected-spiro[piperidine-4,4'-2'-oxo-3',1'-benzooxazine], mp 83°–85° C.

A solution of 20 g of the above compound in 150 ml of methylene chloride and 50 ml of trifluoroacetic acid was stirred for 1 hour at 25° C. Evaporation and treatment of the residue with dilute aqueous sodium hydroxide gave a precipitate, which was filtered to give 11.6 g of tan solid, spiro[piperidine-4,4'-2'-oxo-3',1'-benzooxazine], m.p. 200°–205° C. (dec.).

B. Similarly, following the procedure in Part A of this Preparation, but substituting for N-t-butoxycarbonyl aniline:
t-butoxycarbonyl-4-methylaniline;
t-butoxycarbonyl-3,5-diethoxyaniline;
t-butoxy carbonyl-2-chloroaniline;
t-butoxycarbonyl-3-fluoroaniline;
t-butoxycarbonyl-4-fluoroaniline;
t-butoxycarbonyl-4-chloroaniline;
one obtains;
6'-methyl-spiro[piperidine-4,4'-2'-oxo-3',1'-benzooxazine];
5',7'-diethoxy-spiro[piperidine-4,4'-2'-oxo-3',1'-benzooxazine];
8'-chloro-spiro[piperidine-4,4'-2'-oxo-3',1'-benzooxazine];
5'-fluoro-spiro[piperidine-4,4'-2'-oxo-3',1'-benzooxazine];
6'-fluoro-spiro[piperidine-4,4'-2'-oxo-3',1'-benzooxazine];
6'-chloro-spiro[piperidine-4,4'-2'-oxo-3',1'-benzooxazine].

PREPARATION 2

1'-Methyl-spiro[piperidine-4,4'-2'-oxo-3',1'-benzooxazine]

A. 1.2 g of 1-t-butoxycarbonyl-spiro[piperidine-4,4'-2'-oxo-3',1'-benzooxazine] in 25 ml of dimethylformamide was treated with 0.3 g of 50% sodium hydride dispersion in oil and the mixture was stirred for 1 hour at 25° C. Methyl iodide (0.3 ml) was added and stirring was continued for 1 hour. The solution was poured into water, extracted with ethyl acetate, and the extract was evaporated to an oil which was triturated with hexane. The gummy residue was dissolved in 20 ml. of dichloromethane and 2.7 ml of trifluoroacetic acid and the solution was stirred for 2 hour. The solution was washed with dilute sodium bicarbonate and evaporated to afford 0.6 g of 1'-methyl-spiro[piperidine-4,4'-2'-oxo-3',1'-benzooxazine], m.p. 130°–132° C.

B. Similarly, following the procedure in Part A of this Preparation, but substituting for methyl iodide ethyl iodide, i-propyl iodide or n-butyl iodide, one obtains 1'-ethyl-spiro[piperidine-4,4'-2'-oxo-3',1'-benzooxazine];
1'-i-propyl-spiro[piperidine-4,4'-2'-oxo-3',1'-benzooxazine];
1'-n-butyl-spiro[piperidine-4,4'-2'-oxo-3',1'-benzooxazine].

EXAMPLE 1

Erythro-1'-(2-(benzodioxan-2-yl)-2-hydroxyethyl)-spiro[piperidine-4,4'-2'-oxo-3',1'-benzooxazine]

A. A mixture of 2.2 g of spiro[piperidine-4,4'-2'-oxo-3',1'-benzooxazine] and 1.8 g of erythro-2-epoxybenzodioxane in 30 ml of methanol and 60 ml of toluene was refluxed for 3 hours. The mixture was cooled and filtered to afford 2.7 g of the free base, erythro-1'-(2-(benzodioxan-2-yl)-2-hydroxyethyl)spiro-[piperidine-4,4'-2'-oxo-3',1'-benzooxazine] m.p. 242°–243° C.

The hydrochloride salt was prepared by acidifying a methanol solution of the free base with HCl and precipitation with ether. Recrystallization from isopropanol gave the erythro-HCl salt, mp 275°–277° C.

B. Similarly, following the procedure in Part A of this Example and substituting for spiro[piperidine-4,4'-2'-oxo-3',1'-benzooxazine] the compounds listed in part B of preparation 1, and Parts A and B of Preparation 2, one obtains:

1-(2-(benzodioxan-2-yl)-2-hydroxyethyl)-6'-methyl-spiro[piperidine-4,4'-2'-oxo-3',1'-benzooxazine];
1-(2-(benzodioxan-2-yl)-2-hydroxyethyl)-5',7'-diethoxy-spiro[piperidine-4,4'-2'-oxo-3',1'-benzooxazine];
1-(2-(benzodioxan-2-yl)-2-hydroxyethyl)-8'-chloro-spiro[piperidine-4,4'-2'-oxo-3',1'-benzooxazine];
1-(2-(benzodioxan-2-yl)-2-hydroxyethyl)-5'-fluoro-spiro[piperidine-4,4'-2'-oxo-3',1'-benzooxazine];
2-(benzodioxan-2-yl)-2-hydroxyethyl)-6'-fluoro-spiro[piperidine-4,4'-2'-oxo-3',1'-benzooxazine]; m.p. 166°–168° as the hydrochloride;
2-(benzodioxan-2-yl)-2-hydroxyethyl)-6'-chloro-spiro[piperidine-4,4'-2'-oxo-3',1'-benzooxazine]; m.p. 165°–168° as the hydrochloride;
1-(2-(benzodioxan-2-yl)-2-hydroxyethyl)-1'-methyl-spiro[piperidine-4,4'-2'-oxo-3',1'-benzooxazine]; m.p. 140°–142° as the hydrochloride;
1-(2-(benzodioxan-2-yl)-2-hydroxyethyl)-1'-ethyl-spiro[piperidine-4,4'-2'-oxo-3',1'-benzooxazine];
1-(2-(benzodioxan-2-yl)-2-hydroxyethyl)-1'-n-propyl-spiro[piperidine-4,4'-2'-oxo-3',1'-benzooxazine];
1-(2-(benzodioxan-2-yl)-2-hydroxyethyl)-1'-n-butyl-spiro[piperidine-4,4'-2'-oxo-3',1'-benzooxazine].

C. Substituting for erythro-2-epoxybenzodioxane into the procedure to Part A, the corresponding threo, or erythro mixture one obtains the corresponding threo-2-(benzodioxan-2-yl)-2-hydroxyethyl-spiro[piperidine-4,4'-2'-oxo-3',1'-benzooxazine] and erythro/threo-2-(benzodioxan-2-yl)-2-hydroxyethyl-spiro[piperidine-4,4'-2'-oxo-3',1'-benzooxazine], m.p. 210°–212° as the free base and 173°–175° as the HCl salt.

D. Substituting for erythro-2-epoxybenzodioxane into the procedure of Part A of this Example:
3-phenoxypropyl-1,2-epoxide;
3-(4-methylphenoxy)propyl-1,2-epoxide;
3-(2,6-difluorophenoxy)propyl-1,2-epoxide;
one obtains
1-[3-phenoxy-2-hydroxypropyl]-spiro[piperidine-4,4'-2'-oxo-3',1'-benzooxazine], m.p. 263°–265° as the HCl salt;
1-[3-(4-methylphenoxy)-2-hydroxypropyl]-spiro[piperidine-4,4'-2'-oxo-3',1'-benzooxazine];
1-[3-(2,6-difluorophenoxy)-2-hydroxypropyl]-spiro[piperidine-4,4'-2'-oxo-3',1'-benzooxazine].

EXAMPLE 2

1-(2-(benzodioxan-2-yl)ethyl)-spiro[piperidine-4,4'-2'-oxo-3',1'-benzooxazine] and its salt A. A solution of 1.4 g of the spiro[piperidine-4,4'-2'-oxo-3',1'-benzooxazine] nd 1.25 g of 2-(benzodioxan-2-yl)ethyl bromide in 40 ml of dimethylformamide and 5 ml of triethylamine was heated at 60° C. for 5 hours. The mixture was poured into water and extracted with dichloromethane. The extract was washed with water two times, dried, and evaporated to afford 0.8 g of the free base, 1-(2-(benzodioxan-2-yl)ethyl)spiro[piperidine-4,4'-2'-oxo-3',1'-benzooxazine]; m.p. 65°–70° C. The hydrochloride salt, prepared in the usual way had m.p. 238°–240° C.

B. Similarly, following the procedure in Part A of this Example but substituting for
2-(benzodioxan-2-yl)ethyl bromide;
benzodioxan-2-ylmethyl bromide;
3-(benzodioxan-2-yl)-n-propyl bromide; and
4-(benzodioxan-2-yl)-n-butyl bromide,
one obtains
1-(benzodioxan-2-ylmethyl)-spiro[piperidine-4,4'-2'-oxo-3',1'-benzooxazine]; m.p. 250°–252°, as the hydrochloride;
1-[3-(benzodioxan-2-yl)-n-propyl]-spiro[piperidine-4,4'-2'-oxo-3',1'-benzooxazine];
1-[4-(benzodioxan-2-yl)-n-butyl]-spiro[piperidine-4,4'-2'-oxo-3',1'-benzooxazine],
and their salts.

C. Similarly, substituting for 2-(benzodioxan-2-yl)ethyl bromide into the procedure of Part A of this Example:
3-phenoxypropyl bromide;
3-(4-chlorophenoxy)propyl bromide;
2-(2,4-dimethylphenoxy)ethyl bromide;
3-(3,5-dibromophenoxy)-n-propyl bromide, or
4-(4-cyanophenoxy)-n-butyl bromide;
one obtains
1-(3-phenoxypropyl)-spiro[piperidine-4,4'-2'-oxo-3',1'-benzooxazine];
1-(3-(4-chlorophenoxy)propyl)-spiro[piperidine-4,4'-2'-oxo-3',1'-benzooxazine];
1-(2-(2,4-dimethylphenoxy)ethyl)-spiro[piperidine-4,4'-2'-oxo-3',1'-benzooxazine];
(1-3-(3,5-dibromophenoxy)-n-propyl)-spiro[piperidine-4,4'-2'-oxo-3',1'-benzooxazine];
1-(4-(4-cyanophenoxy)-n-butyl)-spiro[piperidine-4,4'-2'-oxo-3',1'-benzooxazine].

EXAMPLE 3

1-(2-phenyl-2-oxoethyl)spiro[piperidine-4,4'-2'-oxo-3',1'-benzooxazine] and its salt A solution of 1.4 g of spiro[piperidine-4,4'-2'-oxo-3',1'-benzooxazine] and 1.6 g of phenylacetyl bromide in 10 ml of dimethylformamide, 20 ml of acetonitrile, and 7 ml of triethylamine was stirred for 30 minutes at 25° C. Filtration gave 1.3 g of the free base 1-(2-phenyl-2-oxoethyl)spiro[piperidine-4,4'-2'-oxo-3',1'-benzooxaine], m.p. 190°–195° C. The hydrochloride salt had a m.p. 185°–189° C.

EXAMPLE 4

1-(2-phenyl-2-hydroxyethyl)spiro[piperidine-4,4'-2'-oxo-3',1'-benzooxazine] and its salt The above ketone (1.25 g of free base) was hydrogenated in 75 ml of methanol with 0.5 g of 10% palladium on carbon at 45 psi for 12 hours. Filtration and evaporation gave 1.2 g of the alcohol, 1-(2-phenyl-2-hydroxyethyl)spiro[piperidine-4,4'-2'-oxo-3',1'-benzooxazine] m.p. 239°–240° C. The hydrochloride salt had mp 275°–278° C.

EXAMPLE 5

Preparation of Other Compounds of the Invention

A. Using the procedure in Preparation 1, followed by that outlined in Example 1, the following compounds are prepared:

1-[3-(2-cyanophenyl)-2-hydroxypropyl]-spiro-[piperidine-4,4'-2'-oxo-3',1'-benzooxazine], m.p. 237°–238° as the hydrochloride;

1-[3-phenyl-2-hydroxypropyl]-spiro[piperidine-4,4'-2'-oxo-3',1'-benzooxazine], m.p. 263°–265° as the hydrochloride;

1-[3-(2-methoxyphenyl)-2-hydroxypropyl]-7'-fluoro-spiro[piperidine-4,4'-2'-oxo-3',1'-benzooxazine], m.p. 120°–121° as the hydrochloride; and 1-[3-(2-methoxyphenyl)-2-hydroxypropyl]-spiro[piperidine-4,4'-2'-oxo-3',1'-benzooxazine], m.p. 110°–115° as the hydrochloride;

1-[2-(benzodioxan-2-yl)-2-hydroxyethyl]-5'-hydroxyspiro[piperidine-4,4'-2'-oxo-3',1'-benzooxazine], as the hydrochloride;

1-[2-(benzodioxan-2-yl)-2-hydroxyethyl]-5'-methoxyspiro[piperidine-4,4'-2'-oxo-3',1'-benzooxazine]; as the hydrochloride.

B. Using the procedure in Preparation 1, followed by that outlined in Example 2, the following are prepared.

1-[2-(2,4-dimethoxyphenyloxy)ethyl]-spiro[piperidine-4,4'-2'-oxo-3',1'-benzooxazine], m.p. 243°–245° as the hydrochloride;

1-[2-phenyloxyethyl]-spiro[piperidine-4,4'-2'-oxo-3',1'-benzooxazine], m.p. 247°–250° as the hydrochloride;

1-[2,6-dichlorobenzyl]-spiro[piperidine-4,4'-2'-oxo-3',1'-benzooxazine], m.p. 241°–245° as the hydrochloride; and 1-[2-phenylethyl]-spiro[piperidine-4,4'-2'-oxo-3',1'-benzooxazine], m.p. 276°–280° as the hydrochloride.

C. Using the procedure in preparation 1, followed by that outlined in Example 3, the following are prepared:

1-[2-phenyl-2-oxoethyl]-spiro[piperidine-4,4'-2'-oxo-3',1'-benzooxazine], m.p. 190°–195°; 185°–189° as the hydrochloride;

1-[4-(4-fluorophenyl)-4-oxo-n-butyl]-spiro[piperidine-4,4'-2'-oxo-3',1'-benzooxazine], m.p. 225°–228° as the hydrochloride.

D. Using the procedure in Preparation 1, followed by that outlined in Example 3, followed by that in Example 4, the following are prepared:

1-[2-phenyl-2-hydroxyethyl]-spiro[piperidine-4,4'-2'-oxo-3',1'-benzooxazine], m.p. 239°–240°; 275-278 as the hydrochloride;

1-[2-(3-methoxycarbonyl-4-hydroxyphenyl)-2-hydroxyethyl]-spiro[piperidine-4,4'-2'-oxo-3',1'-benzooxazine], m.p. 217°–219° as the hydrochloride; and 1-[2-(3-methanesulfamidophenyl)-2-hydroxyethyl]-spiro[piperidine-4,4'-2'-oxo-3',1'-benzooxazine], m.p. 186°–187° as the hydrochloride.

EXAMPLE 6

Conversion of Free Base to Salt

A. Excess 3% hydrogen chloride in methanol is added to a solution of 1.0 g 1-[2-(benzodioxan-2-yl)-2-hydroxyethyl]-spiro[piperidine-4,4'-2'-oxo-3',1'-benzooxazine] in 20 ml methanol. Diethyl ether is added until precipitation is complete. The product hydrochloride is filtered, washed with ether, air dried and recrystallized.

B. In a similar manner, all compounds of Formula I in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 7

Conversion of Salt to Free Base 1.0 g of 1-[2-(benzodioxan-2-yl)-2-hydroxyethyl]-spiro[piperidine-4,4'-2'-oxo-3',1'-benzooxazine]. Hydrochloride acid suspended in 50 ml of ether is stirred with excess dilute aqueous potassium carbonate solution until the salt is completely dissolved. The organic layer is then separated, washed twice with water, dried over magnesium sulfate and evaporated to yield 1-[2-(benzodioxan-2-yl)-2-hydroxyethyl]-spiro[piperidine-4,4'-2'-oxo-3',1'-benzooxazine] as the free base.

EXAMPLE 8

Direct interchange of acid addition salts

1-[2-(benzodioxan-2-yl)-2-hydroxyethyl]-spiro[piperidine-4,4'-2'-oxo-3',1'-benzooxazine]acetate (1.0 g) is dissolved in 50 ml 50% aqueous sulfuric acid, and the solution evaporated to dryness. The product is suspended in ethanol and filtered, air dried and recrystallized from methanol/acetone to yield 1-[2-(benzodioxan-2-yl)-2-hydroxyethyl]-spiro[piperidine-4,4'-2'-oxo-3',1'-benzooxazine] as the hydrogen sulfate.

In Examples 9–15, the active ingredient is 1-[2-(benzodioxan-2-yl)-2-hydroxyethyl]-1'-methyl-spiro[piperidine-4,4'-2'-oxo-3',1'-benzooxazine] as its hydrochloride; however, other compounds of the invention or their salts may also be used.

EXAMPLE 9

| Ingredients | Quantity per tablet, mgs. |
| --- | --- |
| Active ingredient | 25 |

-continued

| Ingredients | Quantity per tablet, mgs. |
|---|---|
| cornstarch | 20 |
| lactose, spray-dried | 153 |
| magnesium stearate | 2 |

The above ingredients are thoroughly mixed and pressed into single scored tablets.

EXAMPLE 10

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 11

| Ingredients | Quantity per tablet, mgs. |
|---|---|
| Active ingredient | 1 |
| cornstarch | 50 |
| lactose | 145 |
| magnesium stearate | 5 |

The above ingredients are mixed intimately and pressed into single scored tablets.

EXAMPLE 12

| Ingredients | Quantity per tablet, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE 13

| Ingredients | Quantity per tablet, mgs. |
|---|---|
| Active ingredient | 150 |
| lactose | 92 |

The above ingredients are mixed and introduced into a hard-shell gelatin capsule.

EXAMPLE 14

An injectable preparation buffered to a pH of 7 is prepared having the following composition:

| Ingredients | |
|---|---|
| Active ingredient | 0.2 g |
| KH$_2$PO$_4$ buffer (0.4 M solution) | 2 ml |
| KOH (1 N) | q.s. to pH 7 |
| water (distilled, sterile) | q.s. to 20 ml |

EXAMPLE 15

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.,) | 1.0 g |
| flavoring | 0.035 ml |
| colorings | 0.5 mg |
| distilled water | q.s. to 100 ml |

We claim:

1. A compound of the formula and the pharmaceutically acceptable acid addition salts thereof, wherein
$R^1$, $R^2$, $R^3$ and $R^4$ are each independently hydrogen, hydroxy, lower alkyl, lower alkoxy or halo;
R is hydrogen or lower alkyl; and
A is selected from the group consisting of:
2-(benzodioxan-2-yl)-2-hydroxyethyl;
ω-(benzodioxan-2-yl)-alkyl (1–4);
3-(aryloxy)-2-hydroxypropyl, wherein aryloxy is phenyloxy optionally substituted by 1–3 moieties selected from the group consisting of lower alkyl, lower alkoxy, halo, alkylsulfamido, lower alkoxycarbonyl, cyano and trifluoromethyl;
ω-arylalkyl (1–4), wherein aryl is phenyl optionally substituted by 1–3 moieties selected from the group consisting of lower alkyl, lower alkoxy, halo, alkylsulfamido, lower alkoxycarbonyl, cyano and trifluoromethyl;
ω-aryl-ω-oxoalkyl (1–4), wherein aryl is as herein defined;
ω-aryl-ω-hydroxyalkyl (1–4), wherein aryl is as herein defined; and
ω-aryloxyalkyl (1–4), wherein aryloxy is as herein defined.

2. The compound of claim 1 and the pharmaceutically acceptable acid addition salts thereof, wherein A is 2-(benzodioxan-2-yl)-2-hydroxyethyl or ω-(benzodioxan-2-yl)alkyl (1–4).

3. The compound of claim 1 and the pharmaceutically acceptable acid addition salts thereof, wherein A is 3-(aryloxy)-2-hydroxypropyl or ω-aryloxyalkyl (1–4).

4. The compound of claim 1 and the pharmaceutically acceptable acid addition salts thereof, wherein A is ω-aryl-ω-oxoalkyl (1–4); ω-aryl-ω-hydroxyalkyl (1–4) or ω-arylalkyl (1–4).

5. The compound of claim 1 and the pharmaceutically acceptable acid addition salts thereof, wherein $R^1$, $R^2$, $R^3$ and $R^4$ are each independently hydrogen or halo.

6. The compound of claim 1 and the pharmaceutically acceptable acid addition salts thereof, wherein R is hydrogen or methyl.

7. The compound of claim 2 and the pharmaceutically acceptable acid addition salts thereof, wherein $R^1$, $R^2$, $R^3$ and $R^4$ are each independently hydrogen, hydroxy, methoxy or halo; and R is hydrogen or methyl.

8. The compound of claim 3 and the pharmaceutically acceptable acid addition salts thereof, wherein $R^1$, $R^2$, $R^3$ and $R^4$ are each independently hydrogen, hydroxy, methoxy, or halo; and R is hydrogen or methyl.

9. The compound of claim 4 and the pharmaceutically acceptable acid addition salts thereof, wherein $R^1$, $R^2$, $R^3$ and $R^4$ are each independently hydrogen, hydroxy, methoxy, or halo; and R is hydrogen or methyl.

10. The compound of claim 7 and the pharmaceutically acceptable acid addition salts thereof, wherein A is 2-(benzodioxan-2-yl)-2-hydroxyethyl, and R, $R^1$, $R^2$, $R^3$ and $R^4$ are hydrogen, i.e. 1-[2-(benzodioxan-2-yl)-2-hydroxyethylspiro[piperidine-4,4'-2'-oxo-3',1'-benzooxazine)].

11. The compound of claim 7 and the pharmaceutically acceptable acid addition salts thereof, wherein A is 2-(benzodioxan-2-yl)-2-hydroxyethyl, R is methyl, and $R^1$, $R^2$, $R^3$, and $R^4$ are hydrogen, i.e. 1-[2-(benzodioxan-2-yl)-2-hydroxyethyl]-1'-methyl-spiro[piperidine-4,4'-2'-oxo-3',1'-benzooxazine)].

12. The compound of claim 7 and the pharmaceutically acceptable acid addition salts thereof, wherein A is 2-(benzodioxan-2-yl)-2-hydroxyethyl, $R^2$ is chloro, and R, $R^1$, $R^3$, and $R^4$ are hydrogen, i.e. 1-[2-(benzodioxan-2-yl)-2-hydroxyethyl]-6'-chloro-spiro[piperidine-4,4'-2'-oxo-3',1'-benzooxazine].

13. The compound of claim 7 and the pharmaceutically acceptable acid addition salts thereof, wherein A is 2-(benzodioxan-2-yl)-2-hydroxyethyl, $R^2$ is fluoro, and R, $R^1$, $R^3$, and $R^4$ are hydrogen, i.e. 1-[2-(benzodioxan-2-yl)-2-hydroxyethyl]-6'-fluoro-spiro[piperidine-4,4'-2'-oxo-3',1'-benzooxazine].

14. The compound of claim 7 and the pharmaceutically acceptable acid addition salts thereof, wherein A is benzodioxan-2-ylmethyl; and R, $R^1$, $R^2$, $R^3$, and $R^4$ are hydrogen, i.e. 1-[benzodioxan-2-ylmethyl]spiro[piperidine-4,4'-2'-oxo-3',1'-benzooxazine].

15. The compound of claim 7 and the pharmaceutically acceptable acid addition salts thereof, wherein A is 2-(benzodioxan-2-yl)ethyl, and R, $R^1$, $R^2$, $R^3$, and $R^4$ are hydrogen, i.e. 1-[2-(benzodioxan-2-yl)ethyl]spiro[piperidine-4,4'-2'-oxo-3',1'-benzooxazine].

16. The compound of claim 7 and the pharmaceutically acceptable acid addition salts thereof, wherein: A is 2-(benzodioxan-2-yl)-2-hydroxyethyl, $R^2$, $R^3$, $R^4$ and R are hydrogen and $R^1$ is hydroxy, i.e. 1-[2-(benzodioxan-2-yl)-2-hydroxyethyl]-5'-hydroxy-spiro[piperidine-4,4'-2'-oxo-3',1'-benzooxazine].

17. The compound of claim 7 and the pharmaceutically acceptable acid addition salts thereof, wherein: A is 2-(benzodioxan-2-yl)-2-hydroxyethyl, $R^2$, $R^3$, $R^4$ and R are hydrogen and $R^1$ is methoxy, i.e. 1-[2-(benzodioxan-2-yl)-2-hydroxyethyl]-5'-methoxy-spiro[piperidine-4,4'-2'-oxo-3',1'-benzooxazine].

18. The compound of claim 8 and the pharmaceutically acceptable acid addition salts thereof, wherein A is 2-(2,4-dimethoxyphenoxy)ethyl, and R, $R^1$, $R^2$, $R^3$ and $R^4$ are hydrogen; i.e. 1-[2-(2,4-dimethoxyphenoxy)ethyl]-spiro[piperidine-4,4'-2'-oxo-3',1'-benzooxazine].

19. The compound of claim 8 and the pharmaceutically acceptable acid addition salts thereof, wherein A is 2-phenoxyethyl, and R, $R^1$, $R^2$, $R^3$ and $R^4$ are hydrogen; i.e. 1-[2-phenoxyethyl]-spiro[piperidine-4,4'-2'-oxo-3',1'-benzooxazine].

20. The compound of claim 8 and the pharmaceutically acceptable acid addition salts thereof, wherein A is 3-(2-cyanophenoxy)-2-hydroxypropyl, and R, $R^1$, $R^2$, $R^3$ and $R^4$ are hydrogen; i.e. 1-[3-(2-cyanophenoxy)-2-hydroxypropyl]-spiro[piperidine-4,4'-2'-oxo-3',1'-benzooxazine].

21. The compound of claim 8 and the pharmaceutically acceptable acid addition salts thereof, wherein A is 3-phenyl-2-hydroxypropyl and R, $R^1$, $R^2$, $R^3$ and $R^4$ are hydrogen; i.e. 1-[3-phenyl-2-hydroxypropyl]spiro[piperidine-4,4'-2'-oxo-3',1'-benzooxazine].

22. The compound of claim 8 and the pharmaceutically acceptable acid addition salts thereof, wherein A is 3-phenyloxy-2-hydroxypropyl and R, $R^1$, $R^2$, $R^3$ and $R^4$ are hydrogen; i.e. 1-[3-phenyloxy-2-hydroxypropyl]-spiro[piperidine-4,4'-2'-oxo-3',1'-benzooxazine].

23. The compound of claim 8 and the pharmaceutically acceptable acid addition salts thereof, wherein A is 3-(2-methoxyphenoxy)-2-hydroxypropyl, and R, $R^1$, $R^2$, $R^3$ and $R^4$ are hydrogen; i.e. 1-[3-(2-methoxyphenoxy)-2-hydroxypropyl]-spiro[-piperidine-4,4'-2'-oxo-3',1'-benzooxazine].

24. The compound of claim 9 and the pharmaceutically acceptable acid addition salts thereof, wherein A is 2-phenyl-2-oxoethyl, and R, $R^1$, $R^2$, $R^3$ and $R^4$ are hydrogen; i.e. 1-[2-phenyl-2-oxoethyl]-spiro[piperidine-4,4'-2'-oxo-3',1'-benzooxazine].

25. The compound of claim 9 and the pharmaceutically acceptable acid addition salts thereof, wherein A is 4-(4-fluorophenyl)-4-oxo-n-butyl, and R, $R^1$, $R^2$, $R^3$, and $R^4$ are hydrogen; i.e. 1-[4-(4-fluorophenyl)-4-oxo-n-butyl]-spiro[piperidine-4,4'-2'-oxo-3',1'-benzooxazine].

26. The compound of claim 9 and the pharmaceutically acceptable acid addition salts thereof, wherein A is 2-phenyl-2-hydroxyethyl and R, $R^1$, $R^2$, $R^3$, and $R^4$ are hydrogen; i.e. 1-[2-phenyl-2-hydroxyethyl]spiro[-piperidine-4,4'-2'-oxo-3',1'-benzooxazine].

27. The compound of claim 9 and the pharmaceutically acceptable acid addition salts thereof, wherein A is 2-(3-methanesulfamidophenyl)-2-hydroxyethyl, and R, $R^1$, $R^2$, $R^3$ and $R^4$ are hydrogen;, i.e. 1-[3-(3-methanesulfamidophenyl)-2-hydroxyethyl]-spiro[-piperidine-4,4'-2'-oxo-3',1'-benzooxazine].

28. The compound of claim 9 and the pharmaceutically acceptable acid addition salts thereof, wherein A is 2-(4-hydroxy-3-methoxycarbonylphenyl)-2-hydroxyethyl, and R, $R^1$, $R^2$, $R^3$ and $R^4$ are hydrogen; i.e. 1-[2-(4-hydroxy-3-methoxycarbonylphenyl)-2-hydroxyethyl]-spiro[piperidine-4,4'-2'-oxo-3',1'-benzooxazine].

29. The compound of claim 9 and the pharmaceutically acceptable acid addition salts thereof, wherein A is 2,6-dichlorobenzyl, and R, $R^1$, $R^2$, $R^3$ and $R^4$ are hydrogen; i.e. 1-[2,6-dichlorobenzyl]-spiro[piperidine-4,4'-2'-oxo-3',1'-benzooxazine].

30. The compound of claim 9 and the pharmaceutically acceptable acid addition salts thereof, wherein A is 2-phenylethyl and R, $R^1$, $R^2$, $R^3$ and $R^4$ are hydrogen; i.e. 1-(2-phenylethyl)-spiro[piperidine-4,4'-2'-oxo-3',1'-benzooxazine].

31. A pharmaceutical composition for lowering blood pressure in humans which comprises a therapeutically effective hypotensive amount of a compound of claim 1 or a pharmaceutically acceptable acid addition salt thereof in admixture with a pharmaceutically acceptable excipient.

32. A method for lowering blood pressure in humans which method comprises administering to a subject in need of such treatment a therapeutically effective amount of, or a pharmaceutical composition containing a therapeutically effective amount of, the compound of claim 1 or a pharmaceutically acceptable acid addition salt thereof.

* * * * *